(12) United States Patent
West et al.

(10) Patent No.: US 7,565,317 B1
(45) Date of Patent: Jul. 21, 2009

(54) SYSTEM AND METHOD FOR DISPLAYING MARKET INFORMATION AND ORDER PLACEMENT IN AN ELECTRONIC TRADING ENVIRONMENT

(75) Inventors: Robert A. West, Chicago, IL (US); Michael J. Burns, Riverside, IL (US)

(73) Assignee: Trading Technologies International, Inc., Chicago, IL (US)

( * ) Notice: Subject to any disclaimer, the term of this patent is extended or adjusted under 35 U.S.C. 154(b) by 271 days.

(21) Appl. No.: 11/321,831

(22) Filed: Dec. 29, 2005

(51) Int. Cl.
*G06Q 40/00* (2006.01)
(52) U.S. Cl. .......................... 705/37; 705/35; 705/36 R
(58) Field of Classification Search .................. 705/35, 705/36 R, 37
See application file for complete search history.

(56) References Cited

U.S. PATENT DOCUMENTS 7,228,289 B2 * 6/2007 Brumfield et al. ............. 705/35

OTHER PUBLICATIONS

Butcher, Mike. "Mobile Stock Exchange". Irish Times. Dublin: Nov. 19, 2004. p. 8.*
Skertic, Mark. "Chicago Futures Exchanges Rev Up for Global Competition". Knight Ridder Tribune Business News. Washington: Feb. 8, 2004, p. 1.*
Schmerken, Ivy. "CBOE Bets Streaming Quotes Will Cool ISE". Wall Street & Technology. New York: Jul. 2003, p. 41.*

* cited by examiner

*Primary Examiner*—Lalita M Hamilton
(74) *Attorney, Agent, or Firm*—McDonnell Boehnen Hulbert & Berghoff LLP

(57) ABSTRACT

A system and method are provided for displaying a trading screen and placing an order in an electronic trading environment. The system and method may be used to assist a trader in selecting an item of interest, such as the inside market (best bid and best ask) to be displayed relative to a user configured location on the trading screen, such as the center of the trading screen. In a preferred embodiment, the inside market will stay located relative to center of the trading screen and the price levels associated to the inside market will move as the market conditions fluctuate. Other features and advantages are described herein.

20 Claims, 8 Drawing Sheets

SYSTEM AND METHOD FOR DISPLAYING MARKET INFORMATION AND ORDER PLACEMENT IN AN ELECTRONIC TRADING ENVIRONMENT

FIELD OF INVENTION

The present invention is directed to electronic trading. More specifically, the present invention is directed towards a system and method for assisting a trader in placing orders and displaying market information in an electronic trading environment.

BACKGROUND

An exchange is a central marketplace with established rules and regulations where buyers and sellers, referred to as traders, meet to trade. Some exchanges, referred to as open outcry exchanges, operate using a trading floor where buyers and sellers physically meet on the floor to trade. Other exchanges, referred to as electronic exchanges, operate by an electronic or telecommunications network. An electronic exchange typically provides computerized matching between traders. Some example electronic exchanges include European Exchange ("Eurex"), London International Financial Futures and Options Exchange ("LIFFE"), Chicago Mercantile Exchange ("CME"), and Chicago Board of Trade ("CBOT").

With respect to electronic exchanges, traders connect to an electronic trading platform by way of a communication link through their user terminals. Once connected, traders typically choose which tradeable objects they wish to trade. As used herein, the term "tradeable object" refers to anything that can be traded with a quantity and/or price. It includes, but is not limited to, all types of traded events, goods and/or financial products, which can include, for example, stocks, options, bonds, futures, currency, and warrants, as well as funds, derivatives and collections of the foregoing, and all types of commodities, such as grains, energy, and metals. The tradeable object may be "real," such as products that are listed by an exchange for trading, or "synthetic," such as a combination of real products that is created by the user. A tradeable object could actually be a combination of other tradeable objects, such as a class of tradeable objects.

User terminals (also referred to as client devices) are connected to the electronic trading platform by way of a communication link to facilitate electronic messaging between the trading entities and the exchange. The messaging includes market information that is distributed from the electronic exchange to traders, as well as orders, quotes, acknowledgements, fills, cancels, deletes, cancel and replace, and other well-known financial transaction messages. Although the amount or type of market information published by the exchange often differs, there are some standard pieces of information. For instance, market information usually includes the inside market, which generally refers to the current lowest sell price (also referred to as the best ask) and the current highest buy price (also referred to as the best bid). Market information may also include market depth, which generally refers to quantities available in the market at the price levels other than those corresponding to the inside market. In addition to providing order book information including order price and quantity information, electronic exchanges can offer other types of market information such as the open price, settlement price, net change, volume, last traded price, last traded quantity, and order fill information.

Once the client device receives the market information, it may be displayed on the trading screen. Upon viewing the market information, traders can take certain actions including the actions of sending buy or sell orders to the electronic exchange, adjusting existing orders, deleting orders, or otherwise managing orders. There are a variety of different order types that a trader can enter in the electronic market. Traders may also use software tools to automate these and additional actions.

To profit in today's rapidly moving markets, traders must be able to react quickly and assimilate enormous amounts of data. For example, a trader may wish to review market data, world news, business news, and so on before making trades. Consequently, the trading screen and the tools provided to the trader via a trading screen are extremely important when trading in an electronic trading environment and should reflect a trader's preference or style of trading. Depending on the preference or style of trading, some trading screens are better suited than others.

A conventional market grid window displays the inside market and the market depth of a given commodity in a traditional manner. Specifically, the market grid window displays a first row which contains the inside market information. Typically, the first set of columns of the first row contains the best bid price and quantity, while the second set of columns of the first row contains the best ask price and quantity. And if so desired, the market grid window can also display market depth under the first row. For instance, the bid side market depth is displayed under the best bid price in the first column and the ask side market depth is displayed under the best ask price in the second column. The columns are displayed vertically such that the bid and ask prices descend the grid. The bid prices descend the market grid as the prices decrease and the ask prices also descend the market grid while the prices actually increase.

An advantage of the conventional market grid window is that by displaying the inside market on a single row, many tradeable objects can be displayed on a single screen. Another advantage of the market grid window is that the inside market is always in view in the first row, even if the market is moving up or down in value. It should be understood that the term "market" can refer to the inside market or the last traded price ("LTP"). Unfortunately, displaying the market on a single row makes trading in a fast moving market much more difficult to track. Additionally, the ask prices descend the market grid. Therefore, this screen lacks the intuitiveness required to watch the market flow in up or down directions.

Other trading screens flip the ask side column and place it on top of the bid side column. The advantage of this screen is that the inside market still remains in the center and the ask prices now ascend the market grid as the prices increase, thereby correcting one of the disadvantages of the previous screen. However, this type of trading screen still suffers the same disadvantage as its predecessor, namely, that it can still be difficult to view the flow of the market.

Some other trading screens provide an axis of prices in which quantities may be displayed along side their prices. As the market moves up or down in value, the trader may view the bid and ask indicators as they move relative to the price axis to provide an intuitive view of the market. While there are some tools to keep the market in view (e.g., providing a re-centering option and so on), this type of trading screen can let the market "run away," when the market shifts so rapidly that it disappears from the visible space of the trading screen.

Other trading screens might use an axis of prices, but slowly shift the price axis such that the market is moved back to a user configured location on the screen as the market fluctuates. However, this shifting can actually misrepresent the current flow and condition of the market. For example, as the trading screen slowly shifts the inside market down to a user configured location, the current condition of the market could actually be going up and the trader would not know. Similarly, as the trading screen slowly shifts the inside market up to a user configured location, the current condition of the market could actually be going down. Shifting the market back to a user configured location on the trading screen—sometimes shifting in the proper direction with the market and sometimes shifting opposite of the market—can be unpredictable and may lead to confusion.

Each trading screen has its advantages and its disadvantages, depending on the trader's preference and style of trading. It is therefore desirable to offer traders alternative style trading displays that may be more in tune to their preference or style of trading.

BRIEF DESCRIPTION OF DRAWINGS

Many aspects of the present embodiments may be better understood with reference to the following drawings. The components in the drawings are not necessarily to scale, emphasis instead being placed upon illustrative example embodiments.

DETAILED DESCRIPTION

I. Overview

The present application describes example embodiments that include a method, system for use in displaying market data on a trading screen and placing an order using the trading screen in an electronic exchange. The example trading screen displays the market in a center position (or near the center position) so that the market and price levels around the market can be easily found while still maintaining an intuitive view of the market.

To provide an intuitive view of the market, indicators are used to highlight movement of a value axis. While the market remains centered, the value axis is shown to move relative to the static display of the market. In other words, the market is fixed and according to the market's frame of reference, the value axis is shown to move up or down through the use of indicators, depending on the market's movement.

The example embodiments can be employed to effectively and efficiently place an order in an electronic exchange while overcoming some of the disadvantages of trading screens currently offered to traders. The example embodiment allows a trader to place an order without having a problem of the market "running away." Thus, the trader can easily place an order at the market or at prices around the market. Additionally, through the use of market indicators it will be more predictable and apparent to the trader in which direction the market is moving.

While the example embodiments are described herein with reference to the illustrative embodiments for particular applications, it should be understood that the example embodiments are not limited thereto. Other systems, methods, features, and advantages of the present embodiments will be or become apparent to one with skill in the art upon examination of the following drawings and description. It is intended that all such additional systems, methods, features, and advantages be within the scope of the present invention, and be protected by the accompanying claims.

II. A First Example Trading System

Figure 1:
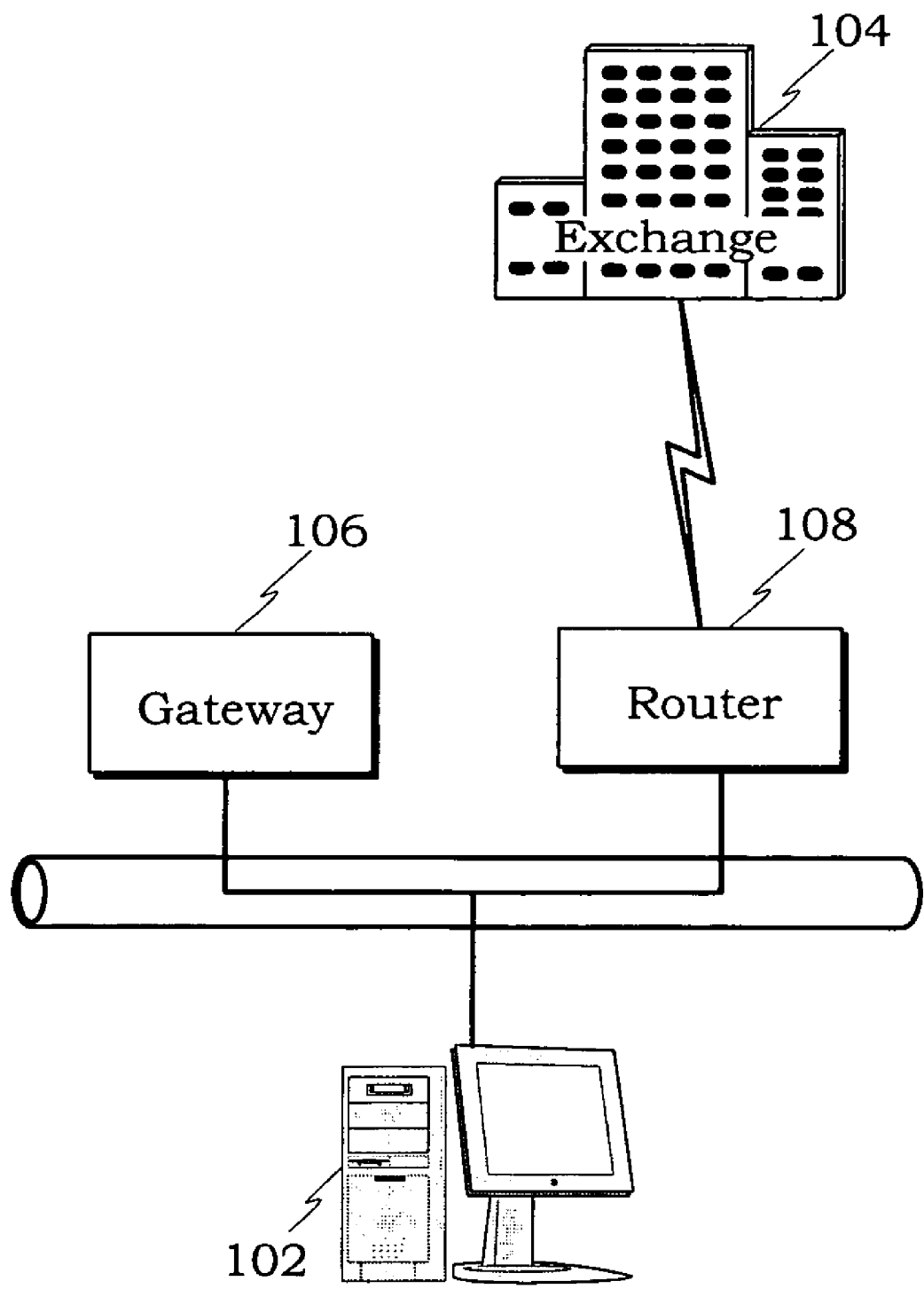
FIG. 1 is a block diagram illustrating a trading system for electronic trading according to an example embodiment, where the trading system includes a trading station where a trader can submit bids and offers for a tradeable object being traded at an electronic exchange.

FIG. 1 illustrates an example electronic trading system in which the example embodiments described herein may be employed. In this example, the system comprises a trading station 102 that accesses an electronic exchange 104 through a gateway 106. Router 108 is used to route messages between the gateway 106 and the electronic exchange 104. The electronic exchange 104 includes a computer process (e.g., the central computer) that matches buy and sell orders sent from the trading station 102 with orders from other trading stations (not shown). The electronic exchange 104 may list one or more tradeable objects for trade. While not shown in the figure for the sake of clarity, the trading system may include other devices that are specific to the client site like middleware and security measures such as firewall, hubs, security managers, and so on, as understood by a person skilled in the art.

The computer employed as the trading station 102 generally can range from a hand-held device, laptop, or personal computer to a larger computer such as a workstation and multiprocessor. Generally, the trading station 102 includes a monitor (or any other output device) and an input device, such as a keyboard and/or a two or three-button mouse to support click based trading, if so desired. One skilled in the art of computer systems will understand that the present example embodiments are not limited to any particular class or model of computer employed for the trading station 102 and will be able to select an appropriate system.

The computer employed as the gateway 106 generally can range from a personal computer to a larger computer. Generally, the gateway 106 may additionally include a monitor (or any other output device), input device (for example, a keyboard, mouse, etc.), and access to a database, if so desired. One skilled in the art of computer systems will also understand that the present example embodiments are not limited to any particular class or model of computer(s) employed for the gateway 106 and will be able to select an appropriate system.

It should be noted that a computer system that may be employed here as a trading station or a gateway generally includes a central processing unit, a memory unit (a primary and/or secondary memory unit), an input interface for receiving data from a communications network, an input interface for receiving input signals from one or more input devices (for example, a keyboard, mouse, etc.), and an output interface for communications with an output device (for example, a monitor). A system bus or an equivalent system may provide communications between these various elements.

It should also be noted that the trading station 102 generally executes application programs resident at the trading station 102 under the control of the operating system of the trading station 102. Also, the gateway 106 executes application programs resident at the gateway 106 under the control of the operating system of the gateway 106. In other embodiments and as understood by a person skilled in the art, the function of the application programs at the trading station 102 may be performed by the gateway 106, and likewise, the function of the application programs at the gateway 106 may be performed by the trading station 102.

The actual electronic trading system configurations are numerous, and a person skilled in the art of electronic trading systems would be able to construct a suitable network configuration. For the purposes of illustration, some example configurations are provided to illustrate where the elements may be physically located and how they might be connected to form an electronic trading system; these illustrations are meant to be helpful to the reader and they are not meant to be limiting. According to one example illustration, the gateway device may be located at the client site along with the trading station, which is usually remote from the matching process at the electronic exchange. According to this instance, the trading station, the gateway, and the router may communicate over a local area network, and the router may communicate with the matching process at the electronic exchange over a T1, T3, ISDN, or some other high speed connection.

In another example illustration, the client site may be located on the actual grounds of the electronic exchange (for example, in the building of the exchange). According to this example illustration, the trading station 102, the gateway 106, and the router 108 may still communicate over a local area network, but the router 108 may communicate with the matching process at the electronic exchange through another connection means besides a T1, T3, or ISDN.

In yet another example illustration, the gateway 106 may be housed at, or near, its corresponding electronic exchange 104. According to this instance, the trading station 102 may communicate with the gateway 106 over a wide area network or through the use of a T1, T3, ISDN, or some other high speed connection.

In another example illustration, the gateway 106 may be located remote from the trading station 102 and remote from the electronic exchange 104, which might be particularly useful in systems that include interconnection of multiple trading networks. Thus, one trading network might have gateway access to an electronic exchange. Then, other trading networks may communicate with the trading network that has gateway access through a T1, T3, ISDN, or some other high speed connection.

III. A Second Example Trading System

Figure 2:
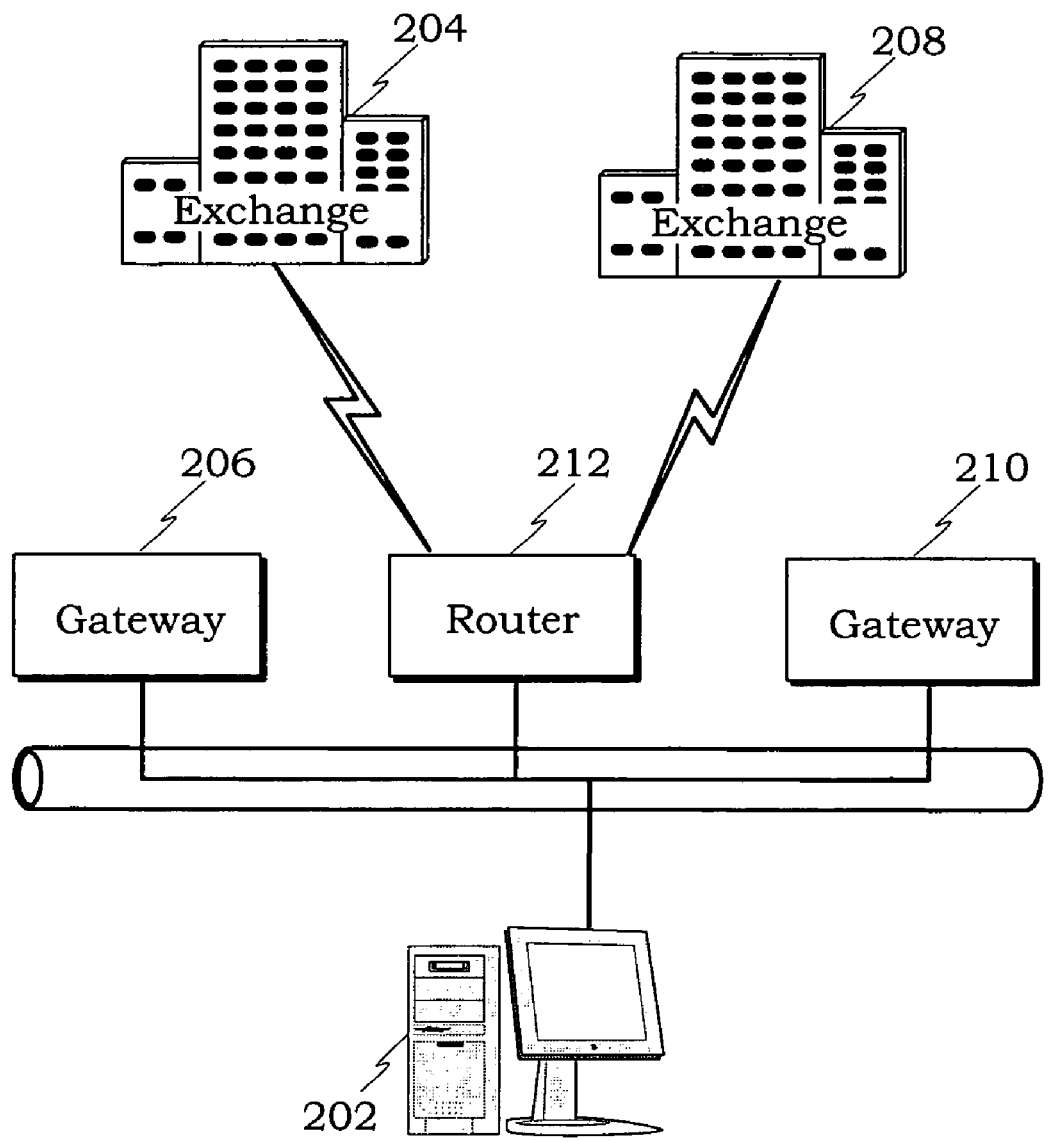
FIG. 2 is a block diagram illustrating a trading system for electronic trading that builds on the trading system shown in FIG. 1 and includes a trading station where a trader can submit bids and offers for a tradeable object being traded at more than one electronic exchange.

FIG. 2 illustrates another example trading system that uses similar computer elements as shown in FIG. 1, in which the example embodiments described herein may be employed to trade at multiple electronic exchanges. The system comprises a trading station 202 that can access multiple electronic exchanges 204 and 208. In this particular embodiment, electronic exchange 204 is accessed through gateway 206 and electronic exchange 208 is accessed through another gateway 210. Alternatively, a single gateway may be programmed to handle more than one electronic exchange. Router 212 is used to route messages between the gateways 206 and 210 and the electronic exchanges 204 and 208. While not shown in the figure, the system may include other devices that are specific to the client site like middleware and security measures like firewalls, hubs, security managers, and so on, as understood by a person skilled in the art. Additional electronic exchanges may be added to the system so that the trader can trade at any number of exchanges, if so desired.

The trading system presented in FIG. 2 provides the trader with the opportunity to trade tradeable objects listed at different electronic exchanges. To some traders, there can be many advantages with a multi-exchange trading environment. For example, a trader could view market information from each tradeable object through one common visual display. As such, price and quantity information from the two separate exchanges may be presented together so that the trader can view both markets simultaneously in the same window.

As indicated earlier, one skilled in the art of electronic trading systems will understand that the present embodiments are not limited to the particular configurations illustrated and described with respect to FIG. 1 and FIG. 2, and will be able to design a particular electronic trading system based on the specific requirements (for example, by adding additional exchanges, gateways, trading stations, routers, or other computers serving various functions like message handling and security). Additionally, several networks, like either of the networks shown in FIG. 1 or FIG. 2, may be linked together to communicatively access one or more electronic exchanges.

IV. An Example Trading System and Function

Figure 3:
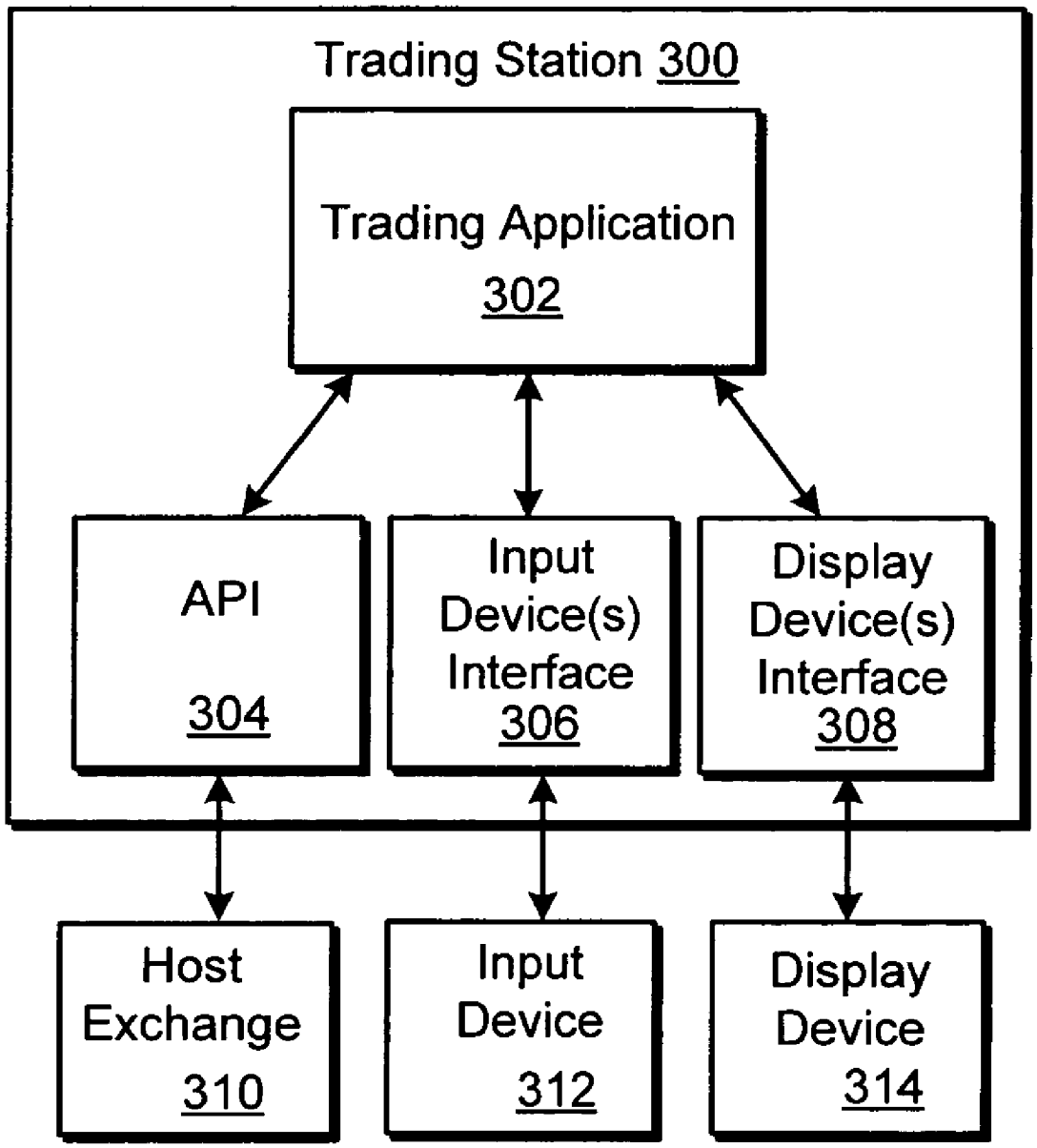
FIG. 3 is a block diagram illustrating various components of an example trading station a trader can use to submit bids and offers for a tradeable object being traded at one or more electronic exchange.

FIG. 3 illustrates an overview of a trading station 300 which is similar to the type of trading stations 102 and 202 shown in FIGS. 1 and 2. Trading station 300 can be any particular type of computing device, examples of which were enumerated above. According to one example embodiment, trading station 300 has a trading application 302 stored in memory that when executed arranges and displays market information on a trading screen that will be described in greater detail below.

Preferably, trading application 302 has access to market information from one or more exchanges 310 through API 304 (or application programming interface), and trading application 302 can also forward transaction information to exchange 310 via API 304. Alternatively, API 304 could be distributed so that a portion of the API rests on the trading station 300 and a gateway similar to the type of gateways 106, 206, and 210 shown in FIG. 1 and FIG. 2, or at the exchange 310. Additionally, trading application 302 may receive signals from input device 312 via input device interface 306 and can be given the ability to send signals to display device 314 via display device interface 308.

Alternatively, the example embodiments described herein may be a separate program from trading application 302, but still stored in memory and executed on the trading station 300. In another alternative embodiment, the preferred embodiments may be a program stored in memory and executed on a device other than trading station 300. Example devices may include a gateway or some other well known intermediary device.

The trading station 300 may use software that creates the trading screen on the trading station 300. The trading screen enables the user to enter and execute orders, obtain market quotes, and monitor positions. The range and quality of features available to the trader on his or her trading screens varies according to the specific software application being run. Example trading screens will be described below in reference to the subsequent figures.

V. View of an Example Trading Screen

Figure 4:
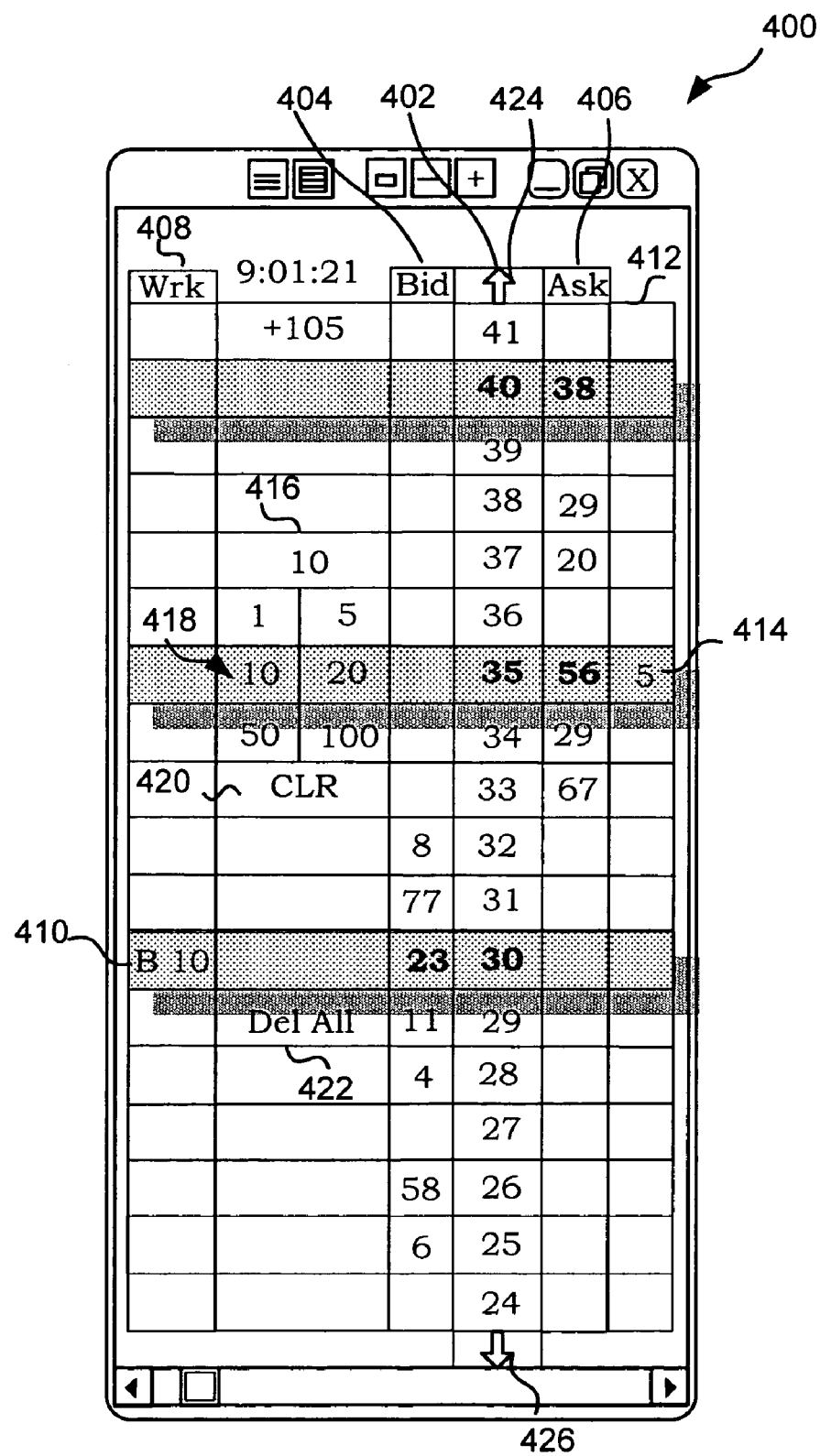
FIG. 4 is an example view of a trading screen with multiple user-placed price movement indicators.

FIG. 4 is an example view of a trading screen 400 with multiple user-placed price movement indicators. Trading screen 400 includes a value axis 402 that indicates values representing prices or some other derivative of price, such as yield, determined for the tradeable object. The prices or some other derivatives of price for the tradeable object are determined based on market data of the tradeable object. While the values are displayed along a vertically oriented axis, the values may be displayed along a horizontally oriented axis or along an axis positioned at some other angle. Once the value axis 402 is generated, quantity and price information contained in the market data feeds corresponding to the tradeable object is received. The received market data is then used to populate the trading screen display against the value axis 402. As new quantity and price information arrive from the electronic exchange, the trading screen 400 is preferably updated to reflect any market changes.

The trading screen 400 also includes a bid quantity column 404 and an ask quantity column 406 that display bid and ask quantity indicators, respectively. The bid and ask quantity indicators are displayed in the locations that correspond to their respective value or price levels along the value axis 402. The best bid and best ask quantity indicators are kept centered on the trading screen 400 by moving the prices of the value axis 402. By looking at the trading screen 400, the trader can quickly locate the inside market, which as mentioned earlier, refers to the highest bid price (best bid) and the lowest ask price (best ask), and in trading screen 400 shown in FIG. 4 corresponds to the prices of "32" and "33" respectively. Further, using the trading screen 400, a trader can view how much quantity is available at various price levels. For example, following the best bid and the best ask, there is a bid quantity of 77 at the price level of "31", and an ask quantity of 29 at the price level of "34". Other levels of market depth are also shown, as illustrated in FIG. 4.

The trading screen 400 also shows additional parameters, such as a working quantity column 408 that illustrates a trader's working order icons. For instance, a working buy order indicator 410 is shown having an order quantity of 10 at the price level of "30". A last traded quantity column 412 is also displayed, which includes the last traded quantity indicator 414 corresponding to the quantity of 5 that was traded at a price level of "35". In addition to the indicators described above, the trading screen 400 includes a default quantity field 416, a number of quantity selection icons 418, a clear all "CLR" icon 420, a delete all order "Del All" icon 422, and market movement indicators 424 and 426. It should be understood that additional indicators could be provided in relation to trading screen 400, and what is actually shown in trading screen 400 may be user configurable.

In the example embodiment, a trader configures the trading screen to display the market in a center position (or near center position) and price movement indicators so that the market and price levels around the market can be easily found and market movement identified. As the market conditions of the tradeable object change, the current best bid and ask quantity indicators remain displayed at the center position (or near center position), such as shown in FIG. 4, while the value axis 402 will move up or down to maintain the market in the center of the screen. Also, the bid and ask quantity values, which correspond to the current inside market, can dynamically change to reflect the current market condition of the tradeable object. It should be understood that the trading screen could be configured to display the market at any location on the trading screen, such as the center, off-center, or some other location on the trading screen 400.

As shown in trading screen 400 in FIG. 4, by using a mouse or keyboard input device, the trader has selected price level "30" associated to a bid quantity of "23," price level "35" associated to an ask quantity of "56," and price level "40" with an ask quantity of "38" to be used as a price movement indicators. Using the user-selected price movement indicators associated with the price levels of "30", "35", and "40" as reference points, the trader can easily recognize and monitor market or price level movements. The price movement indicators are displayed in such a way that the trader can easily differentiate between the selected price levels and the non-selected price levels. Preferably, the price movement indicators can be manually changed or moved to different price levels.

In the example of FIG. 4, the price movement indicators are shown by highlighting the entire row of a price level, while placing a shadow box behind the level as to differentiate between the surrounding price levels. It should also be understood that the price movement indicators associated with price levels "30", "35", and "40" could be displayed in a variety of other ways or at other price levels on trading screen 400. For example, price movement indicators could be displayed by placing a border only around the price level or some other item of interest, changing the color of the price level based on the movement of the market or the relative position to the inside market, or even bolding the price and bid/ask values.

In another example embodiment, a trader may configure the trading screen to automatically place price movement indicators on the trading screen. For example, if a user-placed price movement indicator were to shift out of the visible space of the trading screen, the configured trading screen could automatically associate a price movement indicator with another price level. Additionally, the trader may then select the price movement indicators or possibly move the price movement indicators to another desired price level on the configured trading screen. This feature, along with other options could be configurable by the trader.

FIG. 4 also displays another type of indicator, market movement indicators 424 and 426. In addition to watching the price movement indicators and the inside market to determine if the market has moved up or down, a trader can quickly view a change in the market by watching the market movement indicators 424 and 426. While FIG. 4 displays arrows corresponding to both market movement indicators 424 and 426, only one of them could be displayed to indicate if the market has moved up or down, respectively. Alternatively, as displayed in FIG. 4, two arrows could be displayed, but only one could be highlighted to indicate the direction of the market. The market movement indicators 424 and 426 help the trader to easily see the direction of the market movements, such as if the current inside market prices have shifted up or down corresponding to the previous inside market prices. The market movement indicators 424 and 426 provide a trader with more information regarding the current market conditions. With that added information, a trader can make a more knowledgeable decision about where and when to place subsequent orders in the market.

To enter an order using the trading screen 400, a trader can preset a default quantity at 416 using quantity selection buttons 418, and then use an input device to select a cell in the bid or ask columns, 404 and 406 respectively, corresponding to a desired price level along the value axis 402. For example, if a location in the cell of the bid column 404 associated with the price level of "30" is selected, then a buy order having an order quantity of 10 (determined based on the default quantity shown at 416) would be automatically entered. A working order icon 410, would then be displayed in the working order column 408. A trader could similarly enter a sell order by selecting a location in the cell of the ask column 406 associated with the desired price level along the value axis 402.

According to one example embodiment, a mouse input device could be used to position a cursor over the location or cell and upon selection of the mouse button (either upon the down stroke of the mouse button or upon release of the button, however programmed) an order may be submitted for processing by the trading application. In the example embodiments described above, a trader could distinguish a buy order from a sell order by selecting a location in either the bid column 404 or the ask column 406, respectively. In another example embodiment, buttons on the input device could be programmed so that when a particular button is pressed, it sends a buy order, and when another button is pressed, it sends a sell order.

In yet another example embodiment, the mouse input device could be used to position a cursor over the location or cell and lock onto the desired price level along the value axis 402. As the value axis 402 moves up or down, the mouse cursor would move in relation to the desired price level that was selected by the trader. This feature may be useful for a trader as market data is updated on the trading screen 400 quickly to reflect fast changes in the market, and therefore, prices move and change at a rapid pace. More often than not, it is up to the trader to quickly and accurately move the mouse cursor to a desired price level to place an order, which can sometimes be difficult in a rapidly moving market. The ability to lock onto a desired price level with a mouse cursor will increase the chance of placing an order at the desired price level. This functionality is described in further detail in U.S. patent application Ser. No. 10/729,123, filed on Dec. 5, 2003 and entitled, "Method and System for Displaying a Cursor on a Trading Screen," the contents of which are incorporated herein by reference.

According to another example embodiment, a keyboard may have keys that are associated with the price levels displayed on the trading screen 400, and a trader may initiate an order by selecting a key. Alternatively, a trader may lock onto or select a specific price level on the trading screen using one or more keys on a keyboard. When the market shifts, the trader-selected price will move along with it allowing the trader to see which direction the market shifted, as well as track the trader-selected price.

According to the example embodiment, regardless of the type of input device used, mouse or keyboard, before an order is sent to an electronic exchange, different applications, such as a risk management tool, or yet some other application, could be programmed to process the order and prevent the order from being sent the exchange if certain criteria occur.

VI. View of an Example Trading Screen After the Market has Moved

As the market moves, the user-placed (or automatically placed) price movement indicators shift with the pre-selected price levels so the trader can predictably follow the flow of the market and the specific price levels. In other words, when the price movement indicators shift down, the market has moved up in value; when the price movement indicators shift up, the market has moved down in value. Preferably, by always operating in this fashion, the trader can learn to recognize the changes in the market.

Figure 5:
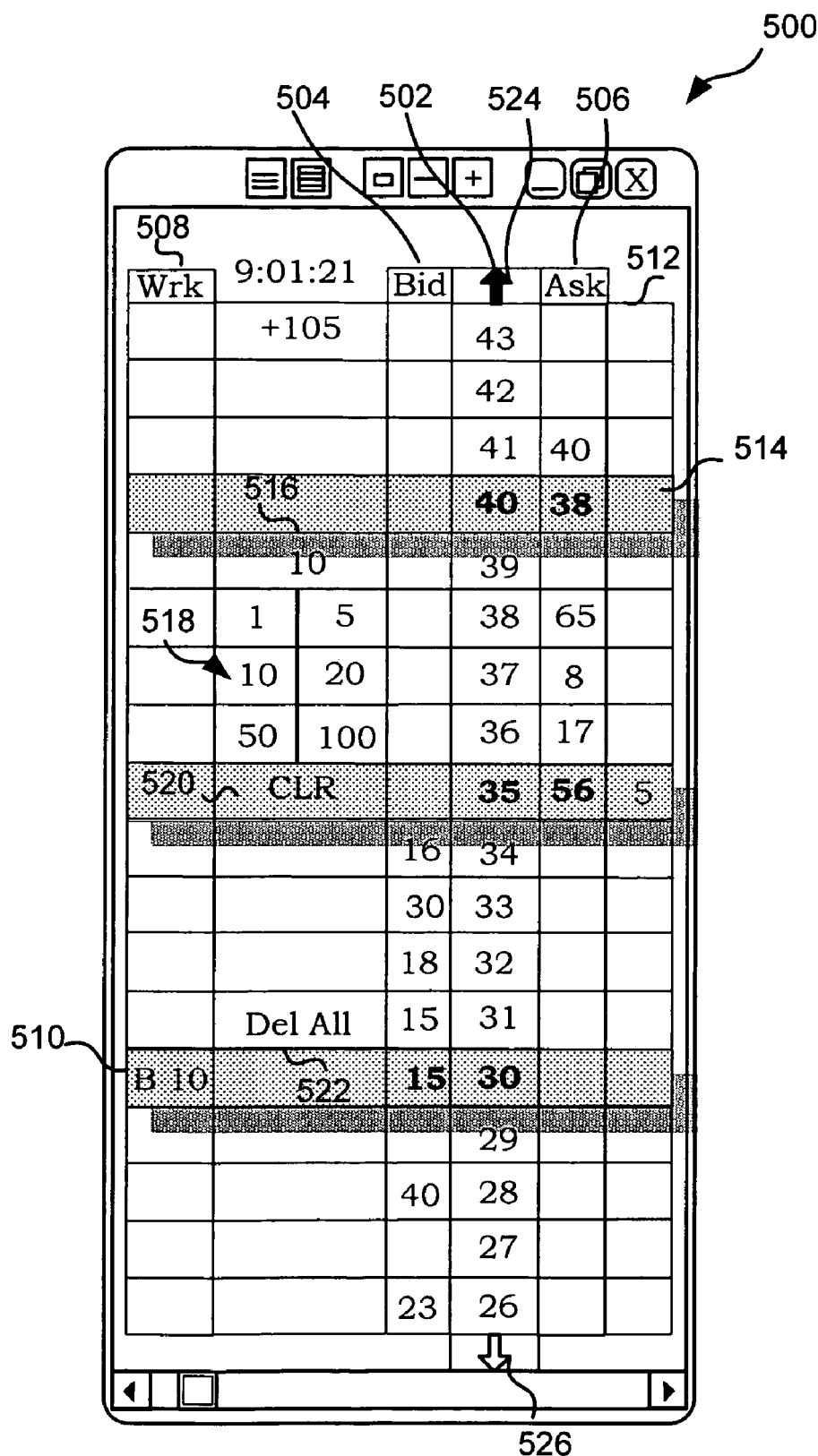
FIG. 5 is an example view of the trading screen with multiple user-placed price movement indicators after the market has moved from the location shown in FIG. 4.

FIG. 5 is a block diagram illustrating a view of trading screen 500 with multiple user-placed price movement indicators after the market has shifted up. Trading screen 500 is the same as trading screen 400 shown in FIG. 4, but the market has changed from time "1" (shown in FIG. 4) to time "2" (shown in FIG. 5). The inside market on trading screen 500 shown in FIG. 5 now corresponds to the best bid and best ask of "34" and "35", respectively. Using the user-placed price movement indicators still associated with the price levels of "30", "35", and "40" as reference points, the trader can easily recognize that the market has shifted up from the previous inside market prices of "32" and "33" shown in FIG. 4. As previously mentioned, if the user-placed price movement indicators were to shift out of the visible space of the trading screen, a trader could simply select another price level, or configure the trading screen to automatically place another price movement indicator on the trading screen. The trader could then move the price movement indicator to a desired price level.

As the market conditions of the tradeable object have changed, the trader will also notice that the best bid and best ask quantity indicators have remained located in the center of the trading screen, even though the market has moved up in value. Further, using the trading screen 500, a trader can view how much quantity is now available at various price levels. For example, following the best bid and the best ask, there is a bid quantity of 30 at the price level of "33", and an ask quantity of 17 at the price level of "36". Other levels of market depth are also shown, as illustrated in FIG. 5.

Trading screen 500 in FIG. 5 also includes market movement indicators 524 and 526. As shown in FIG. 5, market movement indicator 524 is now highlighted to indicate that the current market has moved up. The inside market was previously located at the price levels of the best bid, "32", and the best ask, "33", in FIG. 4, but when compared to the trading screen in FIG. 5, the trader will see that the market shown in trading screen 500 has shifted up two prices levels to "34" and "35", therefore, the market movement indicator 524 is highlighted to indicate this shift to the trader. Likewise, if the current market had moved down, market movement indicator 526 would be highlighted.

One skilled in the art of trading in an electronic trading environment will understand that the example embodiments are not limited to any particular type of indicator to be used to indicate the direction of market movement, and that any indicator could be used to alert the trader in which direction the market has fluctuated. For example, an audio alert could be sounded or a visual alert could be displayed on the screen. It should also be understood that the example embodiments are not limited to a particular number of price movement indicators or that the price movement indicators are limited to specific price levels. For example, price movement indicators may be displayed at price levels in multiples of 5, such as at price levels of "25", "30", "35", and so on.

Figure 6:
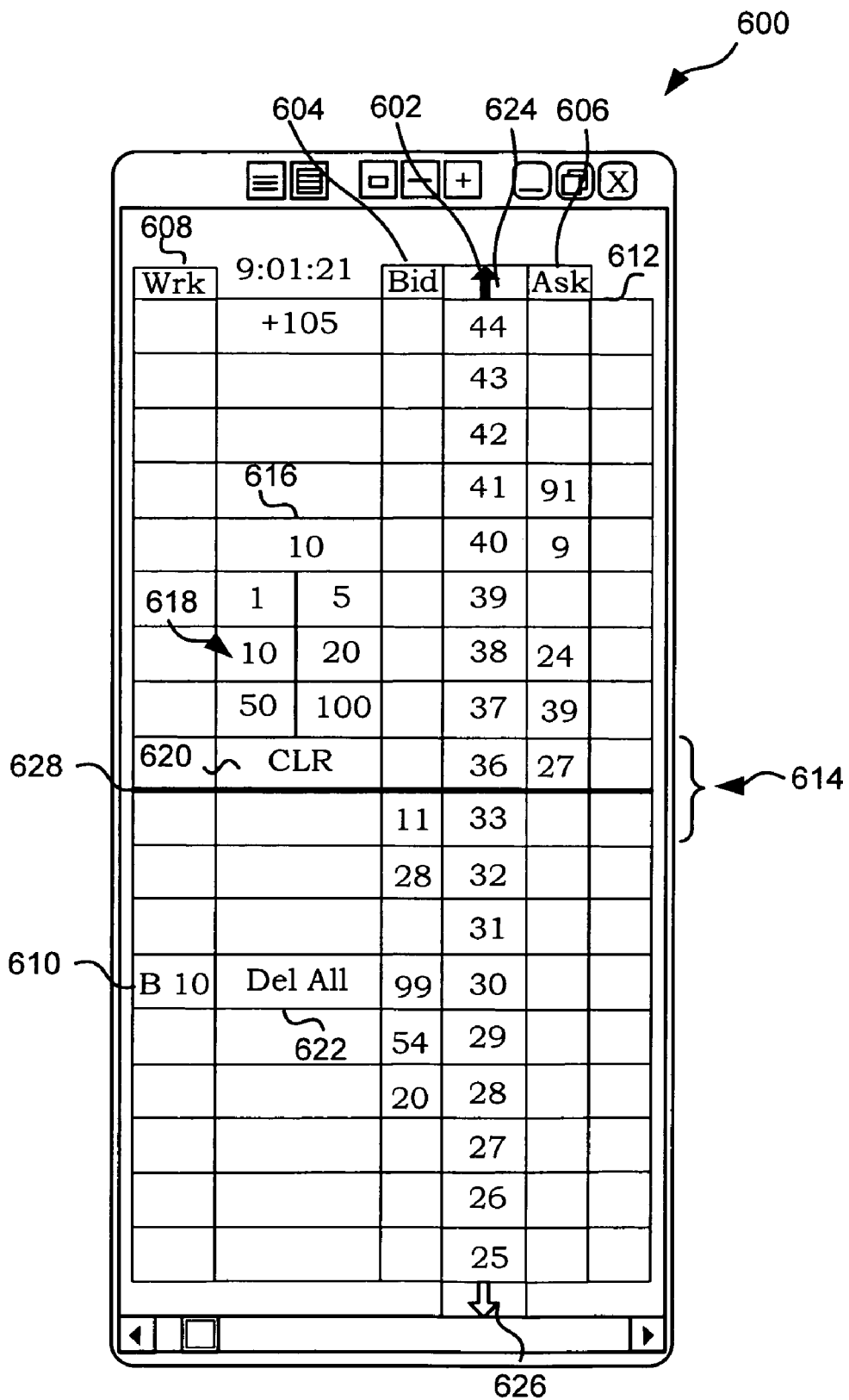
FIG. 6 is an example view of the trading screen where a gap between the inside market prices is collapsed.

There could be circumstances where, based on the market data, the best bid and best ask quantity indicators would not be located at price levels next to each other on the value axis, such that there is a gap between the inside market price levels. Rather than displaying the gap between the current inside market prices and trying to center the prices at or around the center of the trading screen, a trader may wish to view the inside market indicators as if there were no gaps in the market. FIG. 6 is a view of a trading screen where a gap in the inside market is collapsed. Collapsing the gap between the best bid price and the best ask price allows for more of the market depth to be visible to the trader. Additionally, by collapsing the inside market price levels, the market can be maintained in the center portion of the screen (or near center).

A trader may configure the trading screen to collapse other gaps between prices in the market. For example, the gap displayed between the prices of "30" and "32" on the value axis 602, could be collapsed such that the price level of "31" would not be displayed. Alternatively, although not shown in FIG. 6, the gaps could be collapsed until there was a tradeable quantity associated with that price that would consequently trigger a display of the price indicators along the value axis 602. For example, the price level of "31" would be collapsed until there was a tradeable quantity associated with it.

As previously mentioned, a trader may also configure the trading screen to allow the trader to expand or collapse the gaps at any time. For example, a trader could simply select any where on the center line 628, and the prices without any associated quantity, price levels "34", "35", and "36" on the value axis 602, would be expanded and displayed. Once the prices without any associated quantity are displayed, the trader could enter an order into the market at those prices.

Figure 7:
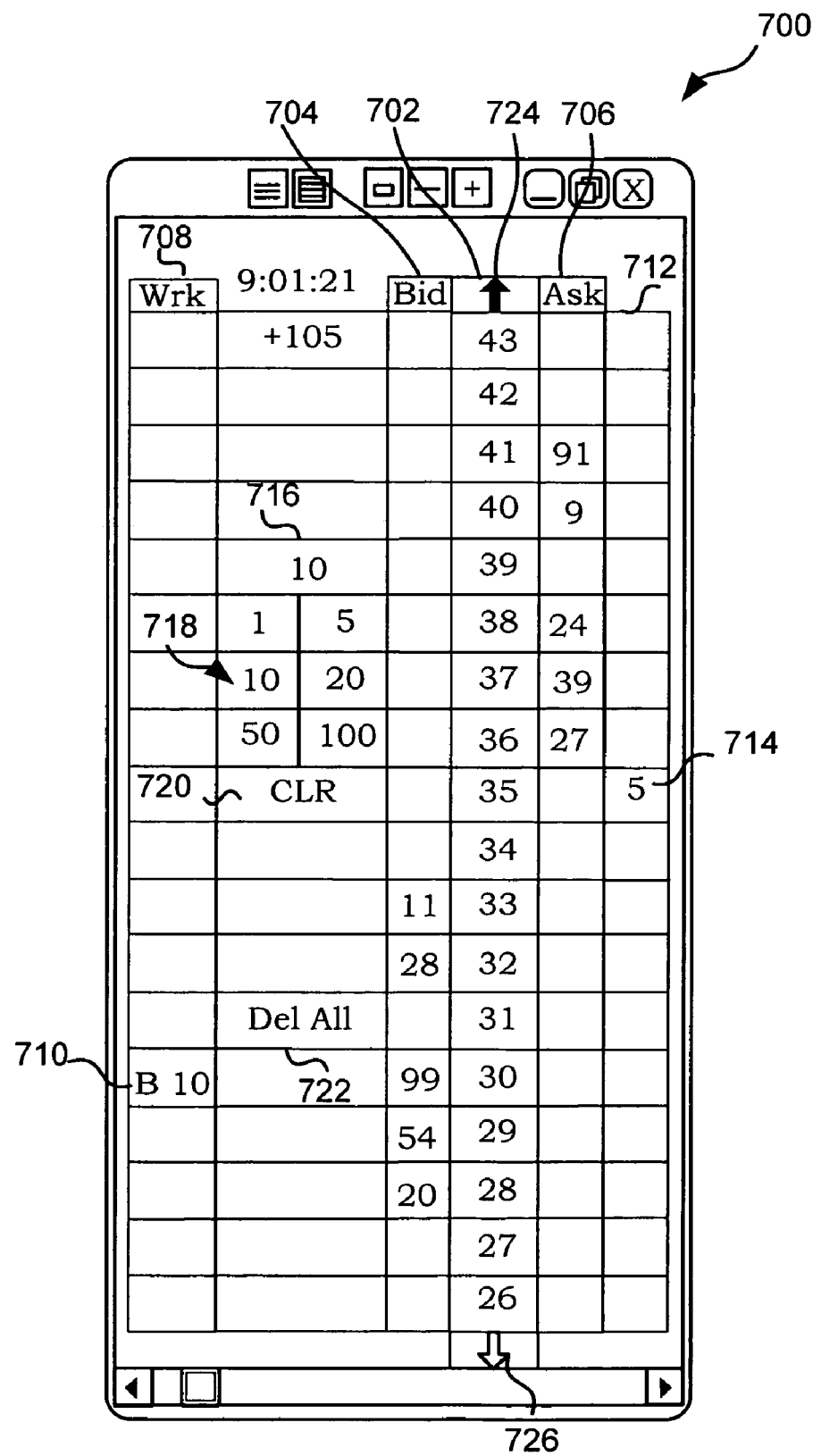
FIG. 7 is an example view of the trading screen showing the gap between the inside market prices.

FIG. 7 is a block diagram illustrating a view of a trading screen after the center line displayed in FIG. 6 is selected, and the gap in the inside market has been expanded. As with the previous figures, the trader can quickly locate the inside market on the trading screen 700 shown in FIG. 7. The inside market, which in the example shown in FIG. 7 now corresponds to the best bid price of "33" with a quantity of 11 and best ask price of "36" with a quantity of 27, therefore creating a gap in the best bid and best ask price. Further, using the trading screen 700, a trader can tell that, while not displayed at the center of the trading screen, the inside market will still be located relative to the center of the trading screen 600.

Figure 8:
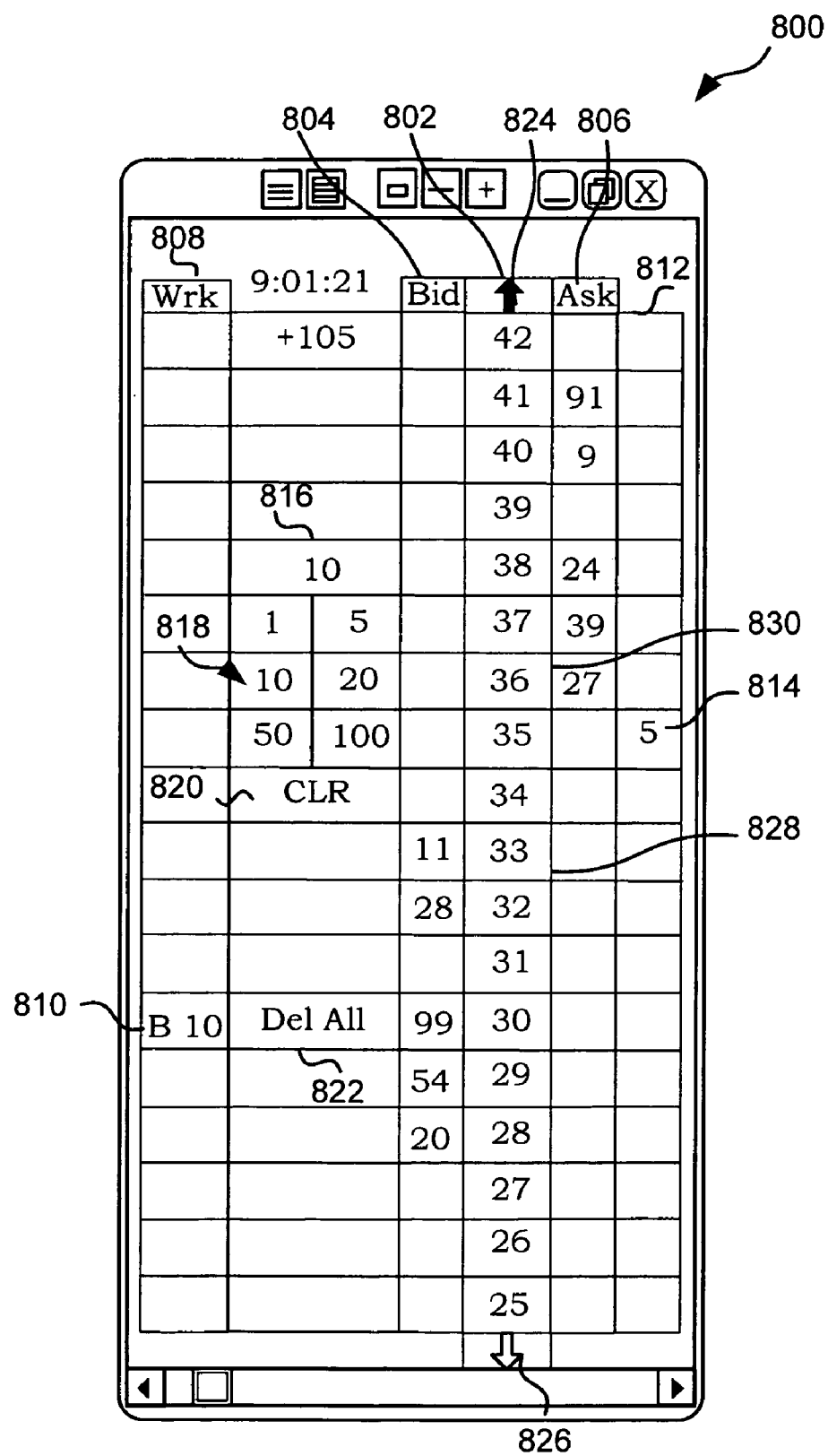
FIG. 8 is an alternative view of the trading screen where there is a gap in the inside market.

According to another example embodiment, instead of displaying the best bid quantity indicator and the best ask quantity indicator around the center of the trading screen, the trader could configure the trading screen to simply display either the best bid quantity indicator or the best ask quantity indicator at or around the center of the trading screen. It should be understood that the trader could configure the trading screen to display anything at the center, for example, the last traded price. FIG. 8 is a block diagram illustrating an alternative view of a trading screen where there is a gap between the inside market prices. As previously described in regards to FIG. 6, there could be circumstances where, based on the market data, the best bid and best ask quantity indicators would not be located at price levels next to each other on the value axis 802, such that there is a gap in the inside market price levels.

Referring to FIG. 8, best bid quantity indicator 828, is centered on the trading screen, while the remaining market data in the value axis 802, bid and ask columns 804 and 806, respectively, are displayed relative to the best bid quantity indicator 828. As with the previous example embodiments, the prices in the value axis 802 move up or down based on the current market conditions, while the selected item of interest, here the best bid quantity indicator 828, remains displayed in a constant position on the trading screen, shown in FIG. 8 at the center of the trading screen. Likewise, the best ask quantity indicator 830 could be centered on the trading screen and the remaining market data could be shifted down and displayed relative to the best ask quantity indicator 830.

CONCLUSION

The example embodiments discussed above described a trading screen that allow traders to place and display price movement indicators while providing an intuitive view of the market. To provide an intuitive view, the market is displayed in the center position (or near the center position) so that the market and price levels around the market can be easily found and the price movement indicators are used to highlight movement of the value axis. While the market remains centered, the value axis is shown to move relative to the static display of the market.

Along with increasing the predictability of which direction the market is moving, price movement indicators allow the trader to track specific price levels on the trading screen. The example embodiments also allow traders to place an order without having a problem of the market "running away." Thus, the trader can easily place an order at the market or at prices around the market.

The above description of the preferred embodiments, alternative embodiments, and specific examples, are given by way of illustration and should not be viewed as limiting. Further, many changes and modifications within the scope of the present embodiments may be made without departing from the spirit thereof, and the present invention includes such changes and modifications.

It will be apparent to those of ordinary skill in the art that methods involved in the system and method for assisting a trader in placing an order in an electronic trading environment may be embodied in a computer program product that includes one or more computer readable media. For example, a computer readable medium can include a readable memory device, such as a hard drive device, a CD-ROM, a DVD-ROM, or a computer diskette, having computer readable program code segments stored thereon. The computer readable medium can also include a communications or transmission medium, such as, a bus or a communication link, either optical, wired or wireless having program code segments carried thereon as digital or analog data signals.

The claims should not be read as limited to the described order or elements unless stated to that effect. Therefore, all embodiments that come within the scope and spirit of the following claims and equivalents thereto are claimed as the invention.

What is claimed is:

1. A method for displaying market information for a tradeable object listed on an electronic exchange, the method comprising:

receiving market data corresponding to the tradeable object via a trading device, the market data comprising substantially real-time order book information for the tradeable object including updates for pending orders for the tradeable object, a last traded price for the tradeable object and an inside market with a highest bid price and a lowest ask price currently available for the tradeable object;

generating a dynamic price axis comprising a plurality of prices that correspond to the tradeable object via the trading device, the plurality of prices arranged in sequence in a range including a highest value to a lowest value along the price axis, the range changeable according to updates for the pending orders;

displaying the plurality of prices of the dynamic price axis in a screen region of a graphical user interface associated with the trading device such that the last traded price, the highest bid price, or the lowest ask price is displayed at a designated location that is substantially fixed in the screen region;

displaying at least one price movement indicator in the screen region of the graphical user interface, the at least one price movement indicator being displayed at a location associated with a particular price of-the plurality of prices of the dynamic price axis; and in response to receiving updated pending orders of the market data, moving, via the trading device, the dynamic price axis with respect to the screen region of the graphical user interface such that the last traded price, the highest bid price, or the lowest ask price remains substantially fixed in the screen region at the designated location, and moving, via the trading device, the location of the at least one price movement indicator with the price axis so that the price movement indicator is being displayed in association with the particular price at a new location in the screen region, the movement of the at least one price movement indicator identifying whether the a market for the tradeable object has moved up or down.

2. The method of claim 1 further comprising the step of designating the locations where the last traded price, the highest bid price, or the lowest ask price are displayed.

3. The method of claim 1 wherein the designated locations are substantially in the center of the screen region of the graphical user interface.

4. The method of claim 1 further comprising the step of manually selecting, through an action of a user input device, the particular price at which the price movement indicator is displayed.

5. The method of claim 1 further comprising the step of manually selecting, through an action of a user input device, a plurality of price levels such that a price movement indicator is displayed at each of the plurality of price levels.

6. The method of claim 1 further comprising the step of automatically selecting the particular price at which the price movement indicator is displayed.

7. The method of claim 1 further comprising the step of automatically selecting a plurality of price levels such that a price movement indicator is displayed at each of the plurality of price levels.

8. The method of claim 1 further comprising the step of displaying an order entry region comprising a plurality of locations for receiving commands to send trade orders, each location corresponding to the a price along the price axis.

9. The method of claim 8 further comprising the step of setting a plurality of parameters for the trade order and sending the trade order to the electronic exchange in response to a selection of a location of the order entry region by a single action of a user input device.

10. The method of claim 1 further comprising the step of displaying a gap between the highest bid price and a lowest ask price currently available for the tradeable object.

11. The method of claim 1 further comprising the step of displaying an additional market indicator for use in determining whether the inside market has moved up or down in value.

12. A device for displaying market information for a tradeable object listed on an electronic exchange, the method comprising:

an interface for receiving market data corresponding to the tradeable object, the market data comprising substantially real-time order book information for the tradeable object including updates for pending orders for the tradeable object, a last traded price for the tradeable object and an inside market with a highest bid price and a lowest ask price currently available for the tradeable object;

a processor coupled to the interface for generating a dynamic price axis comprising a plurality of prices that correspond to the tradeable object, the plurality of prices arranged in sequence in a range including a highest value to a lowest value along the price axis, the range changing according to updates for the pending orders; and an output display coupled to the processor for displaying the plurality of prices of the dynamic price axis in a screen region of the output display such that the last traded price, the highest bid price, or the lowest ask price is displayed at a designated location that is substantially fixed in the screen region, and for displaying at least one price movement indicator in the screen region, the at least one price movement indicator being displayed at a location associated with a particular price of the plurality of prices of the dynamic price axis;

wherein in response to receiving updated pending orders of the market data, the processor moves the dynamic rice axis with respect to the screen region of the graphical user interface such that the last traded price, the highest bid price, or the lowest ask price remain substantially fixed in the screen region at the designated location, and moving the location of the at least one price movement indicator with the price axis so that the price movement indicator is being displayed in association with the particular price at a new location in the screen region, the movement of the at least one price movement indicator identifying whether the tradeable object has moved up or down.

13. The device of claim 12 wherein the designated locations are substantially in the center of the screen region of the graphical user interface.

14. The device of claim 12 further comprising a user input device for selecting the particular price at which the price movement indicator is displayed.

15. The device of claim 12 further comprising the processor automatically selecting the particular price, based on an algorithm, at which the price movement indicator is displayed.

16. The device of claim 12 further comprising an order entry region comprising a plurality of locations for receiving commands to send trade orders, each location corresponding to the a price along the price axis.

17. The device of claim 12 further comprising a user input device for setting a plurality of parameters for the trade order and sending the trade order to the electronic exchange in response to a selection of a location of the order entry region by a single action of the user input device.

18. The device of claim 12 wherein a gap is displayed in the screen region between the highest bid price and a lowest ask price currently available for the tradeable object.

19. The device of claim 12 wherein an additional market indicator is displayed in the screen region for use in determining whether the inside market has moved up or down in value.

20. A computer readable medium containing program instructions for causing a microprocessor to execute a method for displaying market information for a tradeable object listed on an electronic exchange, comprising:

receiving market data corresponding to the tradeable object via a trading device, the market data comprising substantially real-time order book information for the tradeable object including updates for pending orders for the tradeable object, a last traded price for the tradeable object and an inside market with a highest bid price and a lowest ask price currently available for the tradeable object;

generating a dynamic price axis comprising a plurality of prices that correspond to the tradeable object via the trading device, the plurality of prices arranged in sequence in a range including a highest value to a lowest value along the price axis, the range being variable according to updates for the pending orders;

displaying the plurality of prices of the dynamic price axis in a screen region of a graphical user interface associated with the trading device such that the last traded price, the highest bid price, or the lowest ask price is displayed at a designated location that is substantially fixed in the screen region;

displaying at least one price movement indicator in the screen region of the graphical user interface, the at least one price movement indicator being displayed at a location associated with a particular price of the plurality of prices of the dynamic axis; and in response to receiving updated pending orders of the market data, moving, via the trading device, the dynamic price axis with respect to the screen region of the graphical user interface such that the last traded price, the highest bid price, or the lowest ask price remains substantially fixed in the screen region at the designated location, and moving, via the trading device, the location of the at least one price movement indicator with the price axis so that the price movement indicator is being displayed in association with the particular price at a new location in the screen region, the movement of the at least one price movement indicator identifying whether a market for the tradeable object has moved up or down.

* * * * *